(12) United States Patent
Luboshitz et al.

(10) Patent No.: US 10,682,237 B2
(45) Date of Patent: Jun. 16, 2020

(54) PROSTHESIS FOR REPLACING JOINT IN A HUMAN HAND OR FOOT

(71) Applicant: CMC SERT LTD., Hibat Tzion (IL)

(72) Inventors: Shmuel Luboshitz, Hibat Tzion (IL); Avraham Shekalim, Nesher (IL)

(73) Assignee: CMC SERT LTD., Hibat Tzion (IL)

( * ) Notice: Subject to any disclaimer, the term of this patent is extended or adjusted under 35 U.S.C. 154(b) by 115 days.

(21) Appl. No.: 15/753,975

(22) PCT Filed: Sep. 5, 2016

(86) PCT No.: PCT/IB2016/055302
§ 371 (c)(1),
(2) Date: Feb. 21, 2018

(87) PCT Pub. No.: WO2017/037686
PCT Pub. Date: Mar. 9, 2017

(65) Prior Publication Data
US 2018/0250139 A1 Sep. 6, 2018

Related U.S. Application Data

(60) Provisional application No. 62/213,732, filed on Sep. 3, 2015, provisional application No. 62/255,540, filed on Nov. 16, 2015.

(51) Int. Cl.
*A61F 2/42* (2006.01)
*A61F 2/30* (2006.01)

(52) U.S. Cl.
CPC ......... *A61F 2/4241* (2013.01); *A61F 2/4225* (2013.01); *A61F 2002/3085* (2013.01);
(Continued)

(58) Field of Classification Search
CPC ............... A61F 2/4241; A61F 2/4261; A61F 2/4264–4297; A61F 2/4225;
(Continued)

(56) References Cited

U.S. PATENT DOCUMENTS 3,990,116 A * 11/1976 Fixel ..................... A61F 2/3836
623/23.41
4,129,903 A * 12/1978 Huggler ................ A61F 2/3601
606/67

(Continued)

*Primary Examiner* — Alvin J Stewart
(74) *Attorney, Agent, or Firm* — Mark M. Friedman

(57) ABSTRACT

A prosthesis for replacing a joint between a first bone and a second bone in a human hand or foot includes first and second rigid blocks (110, 120) interconnected by a flexible bridging structure (130). In certain embodiments, the flexible bridging structure employs a helical spring oriented with its central axis aligned with a central axis of a bone anchor portion of the first rigid block. One or more shear-limiting element (101, 140) is deployed within an internal volume of the helical spring (130) to limit an extent of shear deformation applied to the helical spring. Other aspects of the invention relate to adjustable bone-abutment flanges, an alternative bridging structure employing a helically-twisted leaf spring, and a structure and method for bridging between the first metacarpal and the scaphoid in case of removal of the trapezium from the hand.

21 Claims, 13 Drawing Sheets

(52) U.S. Cl.
CPC ............... *A61F 2002/30462* (2013.01); *A61F 2002/30507* (2013.01); *A61F 2002/30566* (2013.01); *A61F 2002/30571* (2013.01); *A61F 2002/4258* (2013.01); *A61F 2002/4279* (2013.01)

(58) Field of Classification Search
CPC .... A61F 2002/4228–4238; A61F 2002/30566; A61F 2002/30565; A61F 2002/30568; A61F 2002/30563; A61F 2002/3057; A61F 2002/30571; A61F 2002/30574; A61F 2002/30462; A61F 2/08–0811; A61F 2002/0817–0894
See application file for complete search history.

(56) References Cited

U.S. PATENT DOCUMENTS

| | | | | |
|---|---|---|---|---|
| 4,164,793 A * | 8/1979 | Swanson | A61F 2/4261 | 623/21.14 |
| 4,198,712 A * | 4/1980 | Swanson | A61F 2/4261 | 623/21.14 |
| 4,229,840 A * | 10/1980 | Gristina | A61F 2/4261 | 623/21.13 |
| 5,011,497 A * | 4/1991 | Persson | A61F 2/4241 | 623/21.15 |
| 5,062,851 A * | 11/1991 | Branemark | A61F 2/4241 | 623/23.41 |
| 5,423,816 A * | 6/1995 | Lin | A61B 17/7028 | 606/247 |
| 5,534,033 A * | 7/1996 | Simpson | A61F 2/30721 | 623/13.14 |
| 5,879,396 A * | 3/1999 | Walston | A61F 2/4241 | 623/23.41 |
| 6,342,076 B1 * | 1/2002 | Lundborg | A61F 2/30742 | 623/21.15 |
| 6,383,223 B1 * | 5/2002 | Baehler | A61F 2/4241 | 623/16.11 |
| 7,842,091 B2 * | 11/2010 | Johnstone | A61F 2/4261 | 623/13.12 |
| 7,887,586 B2 * | 2/2011 | Linares | A61F 2/0811 | 606/247 |
| 9,381,079 B2 * | 7/2016 | Wolfson | A61F 2/3836 | |
| 2003/0040805 A1 * | 2/2003 | Minamikawa | A61F 2/4241 | 623/23.46 |
| 2005/0113924 A1 * | 5/2005 | Buttermann | A61B 17/1671 | 623/17.13 |
| 2005/0251260 A1 * | 11/2005 | Gerber | A61F 2/441 | 623/17.13 |
| 2006/0241631 A1 * | 10/2006 | Kilburn | A61B 17/92 | 606/86 R |
| 2007/0067037 A1 * | 3/2007 | Studer | A61F 2/4455 | 623/17.13 |
| 2007/0233255 A1 * | 10/2007 | Song | A61F 2/4425 | 623/17.11 |
| 2008/0103601 A1 * | 5/2008 | Biro | A61F 2/44 | 623/17.16 |
| 2010/0070043 A1 * | 3/2010 | Kitchen | A61F 2/4225 | 623/18.11 |
| 2010/0305698 A1 * | 12/2010 | Metzger | A61F 2/3836 | 623/13.12 |
| 2011/0004255 A1 * | 1/2011 | Weiner | A61B 17/1682 | 606/301 |
| 2011/0112652 A1 * | 5/2011 | Hansson | A61F 2/4241 | 623/21.16 |
| 2013/0231744 A1 * | 9/2013 | Taylor | A61F 2/28 | 623/16.11 |
| 2014/0094919 A1 * | 4/2014 | Mantri | A61F 2/442 | 623/17.16 |
| 2015/0025641 A1 * | 1/2015 | Masson | A61F 2/4014 | 623/19.13 |
| 2016/0120639 A1 * | 5/2016 | Murray | A61F 2/389 | 623/13.12 |
| 2016/0302935 A1 * | 10/2016 | Oster | A61F 2/4241 | |
| 2017/0049477 A1 * | 2/2017 | Yeh | A61B 17/68 | |
| 2017/0100251 A1 * | 4/2017 | Ek | A61F 2/30 | |
| 2018/0116819 A1 * | 5/2018 | Maguire | A61F 2/442 | |

\* cited by examiner

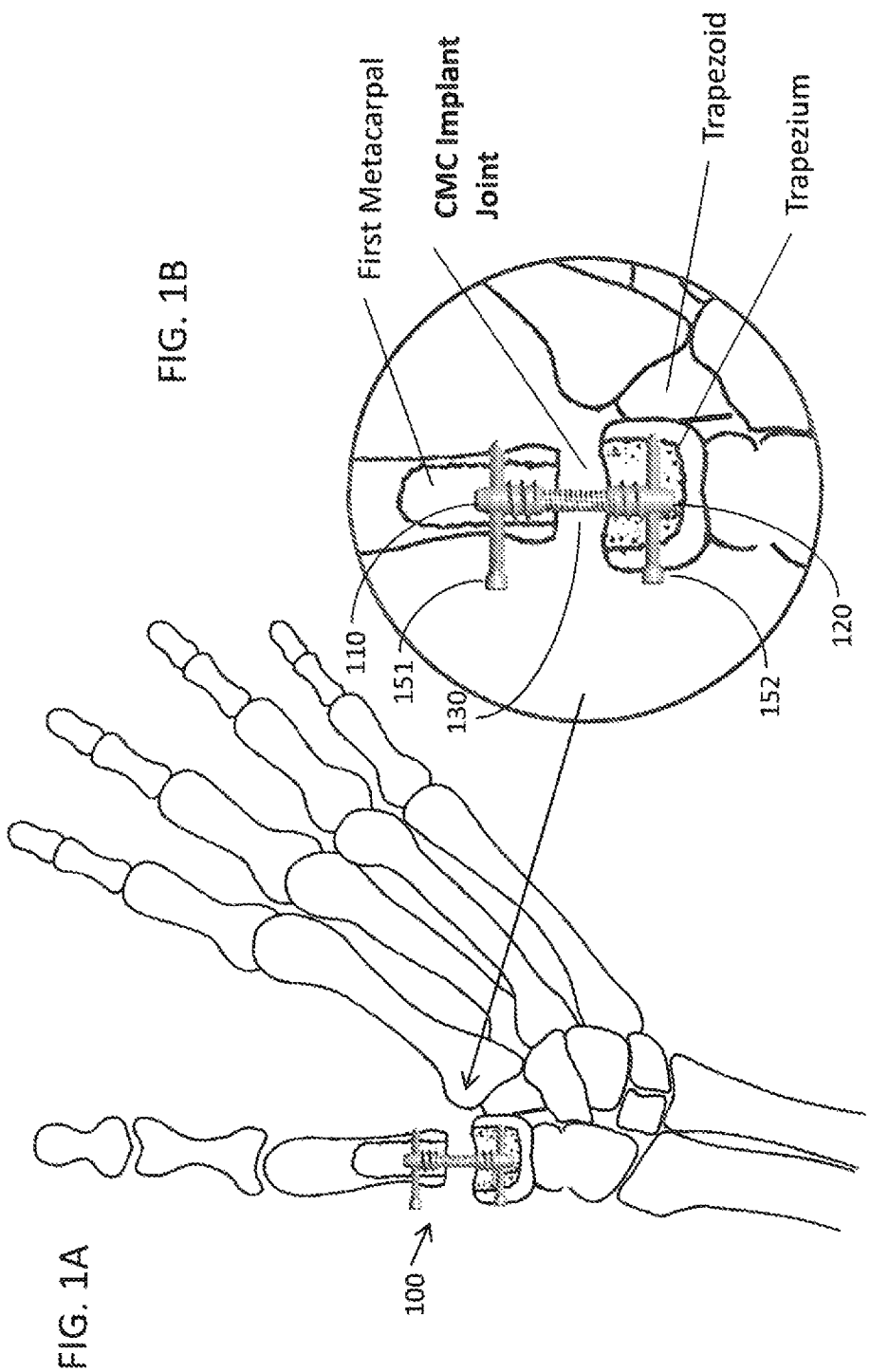

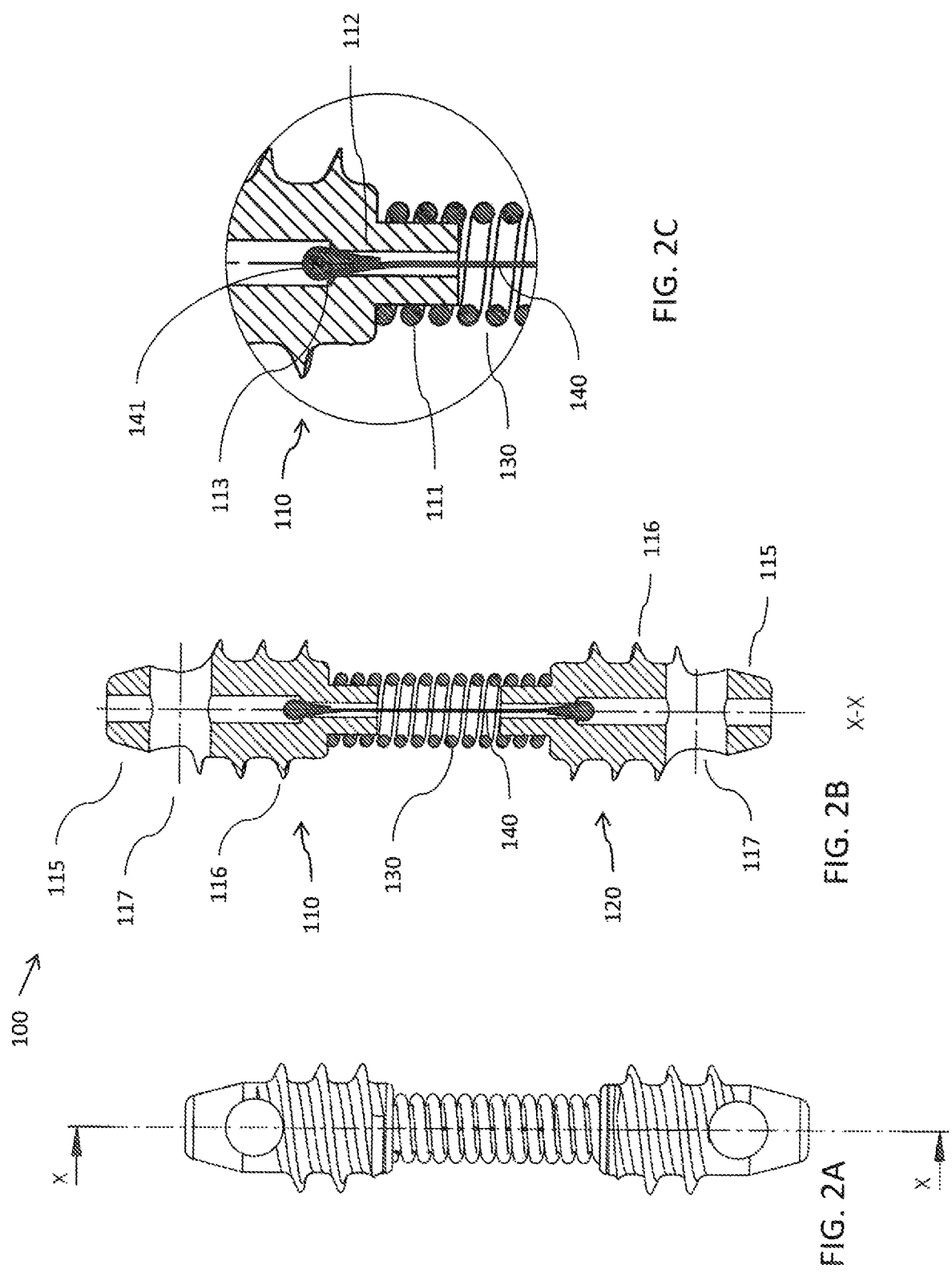

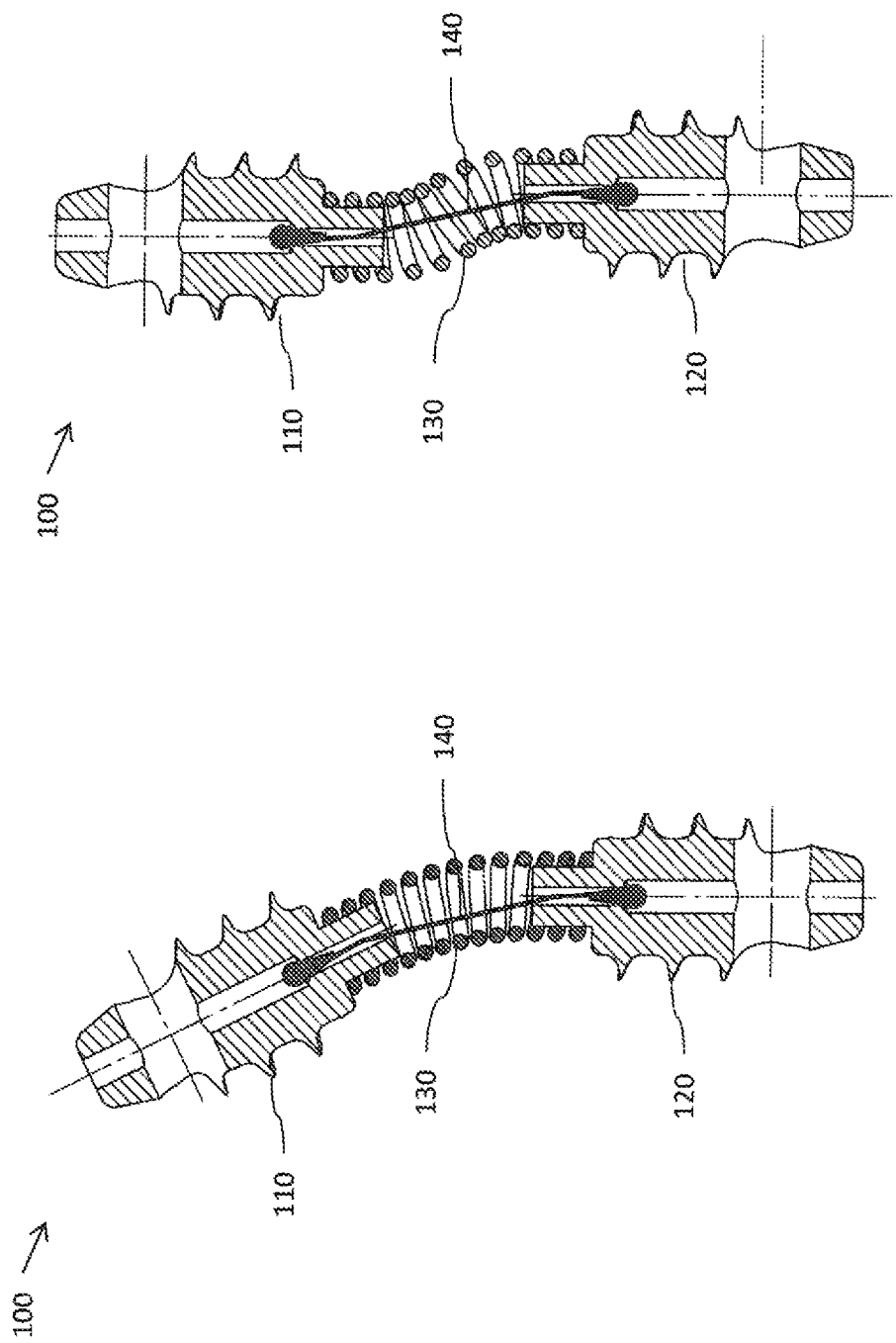

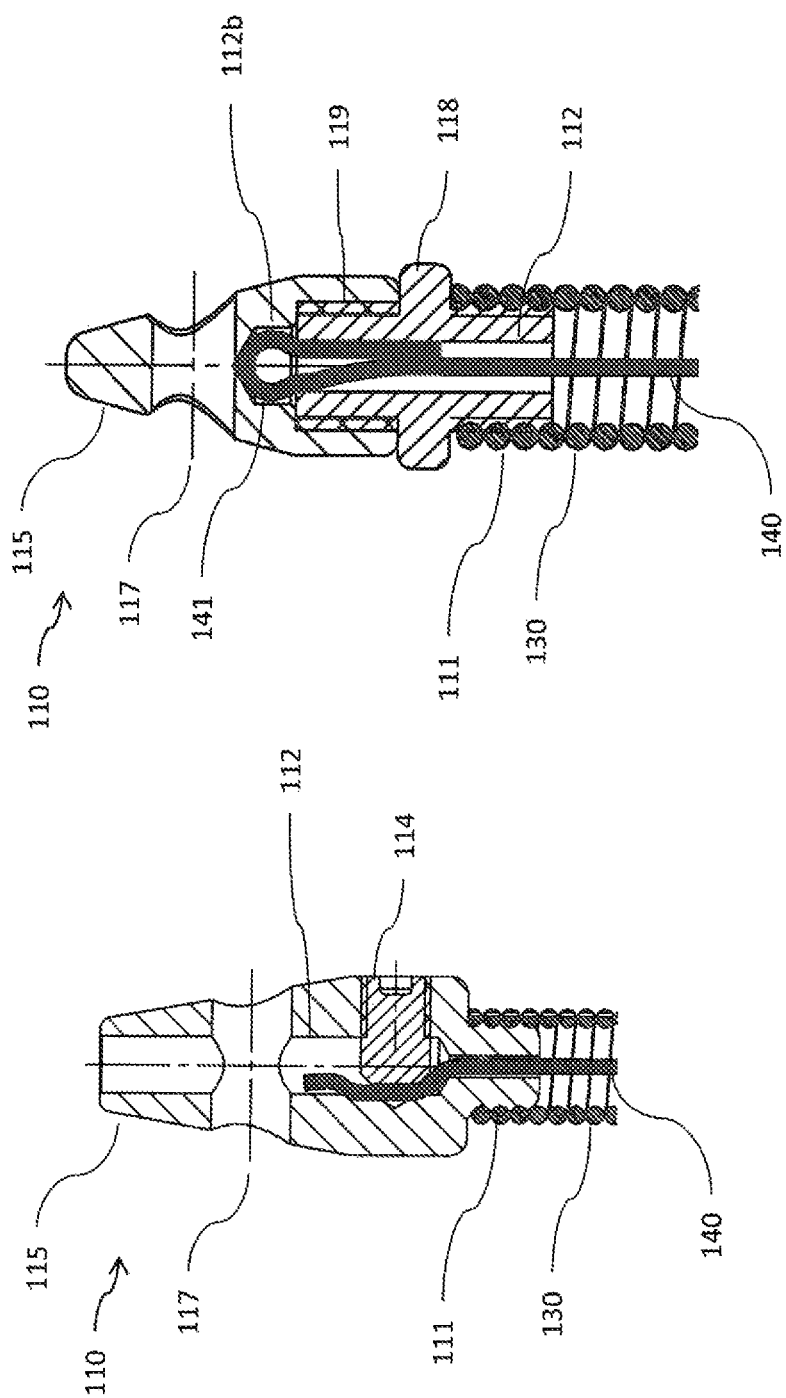

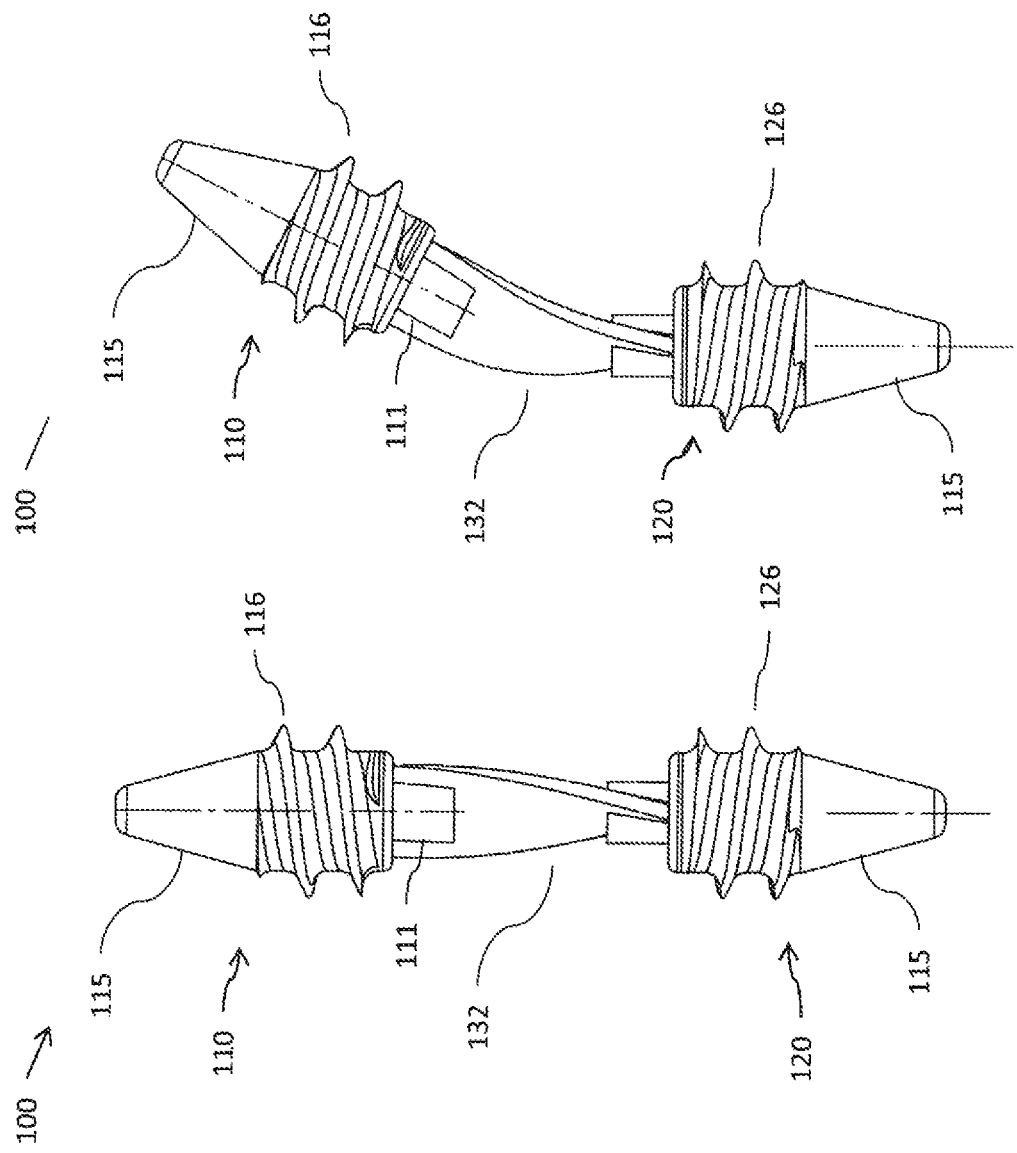

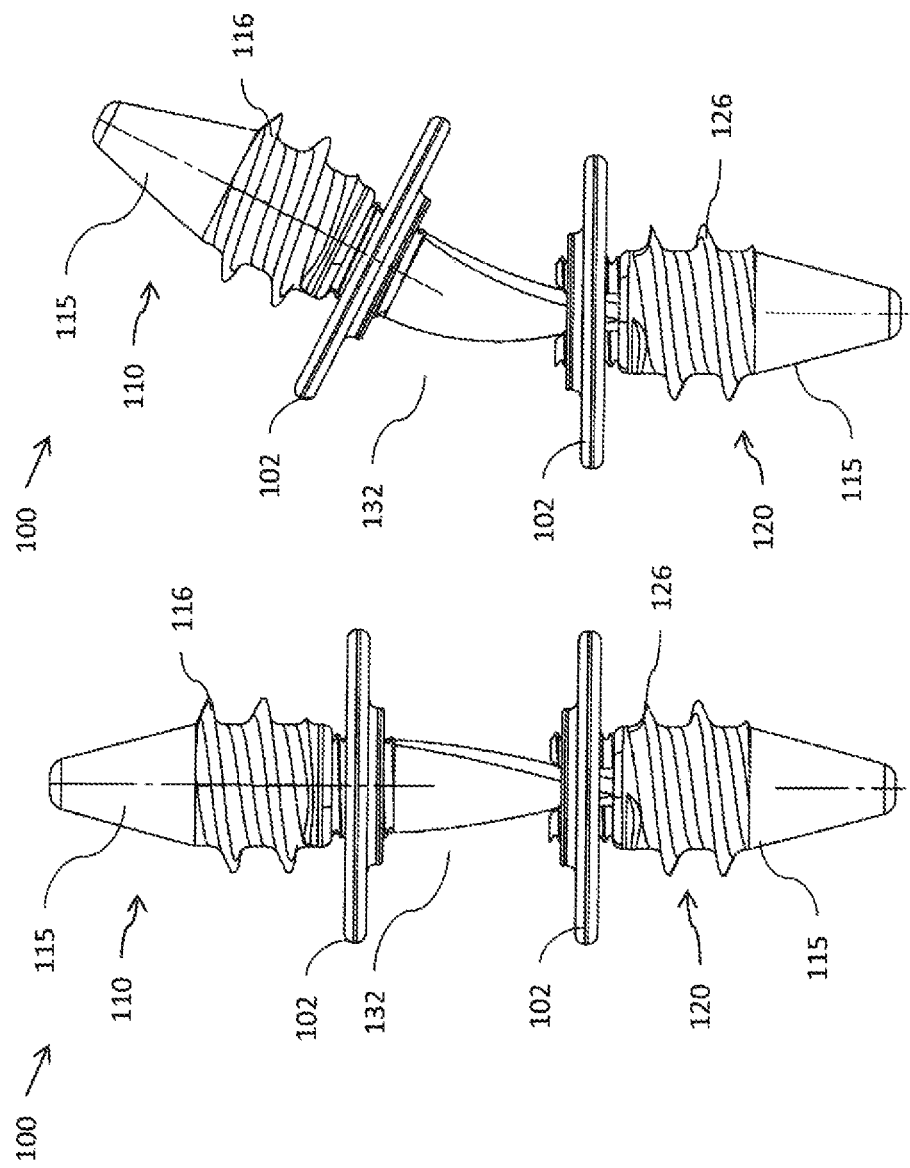

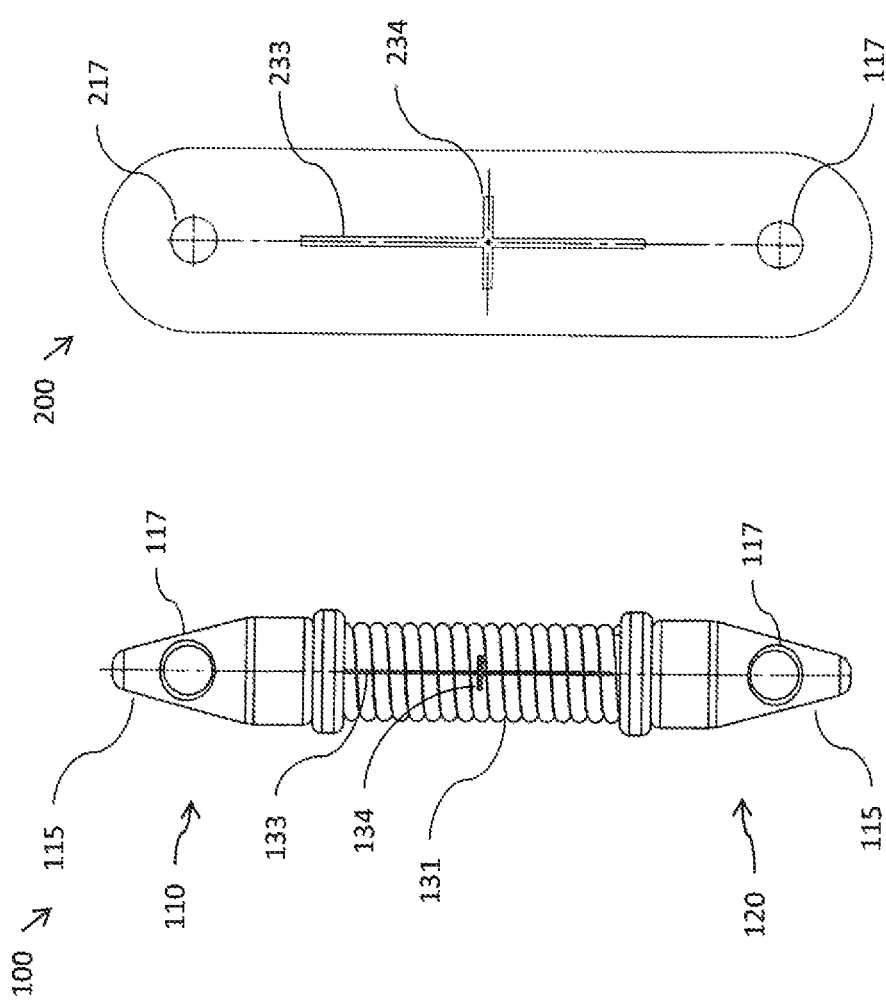

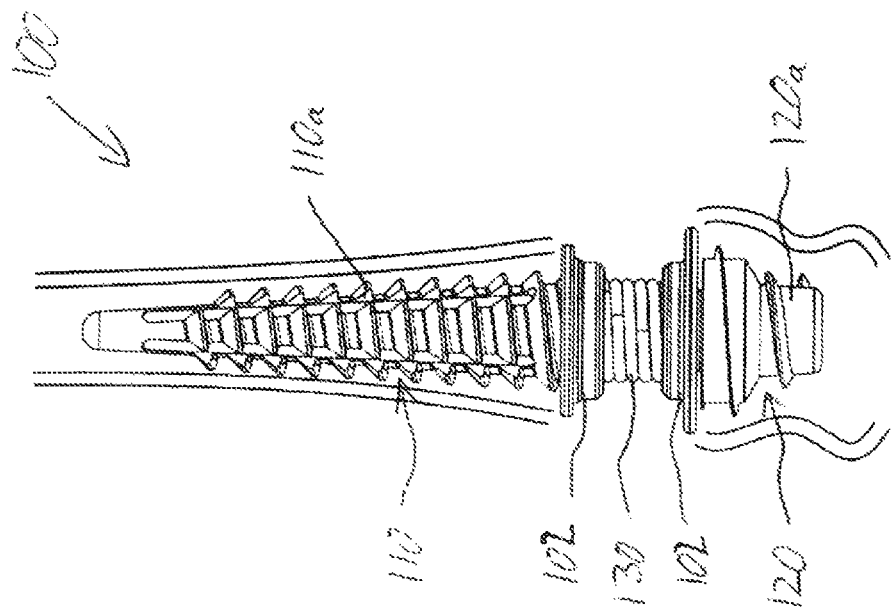
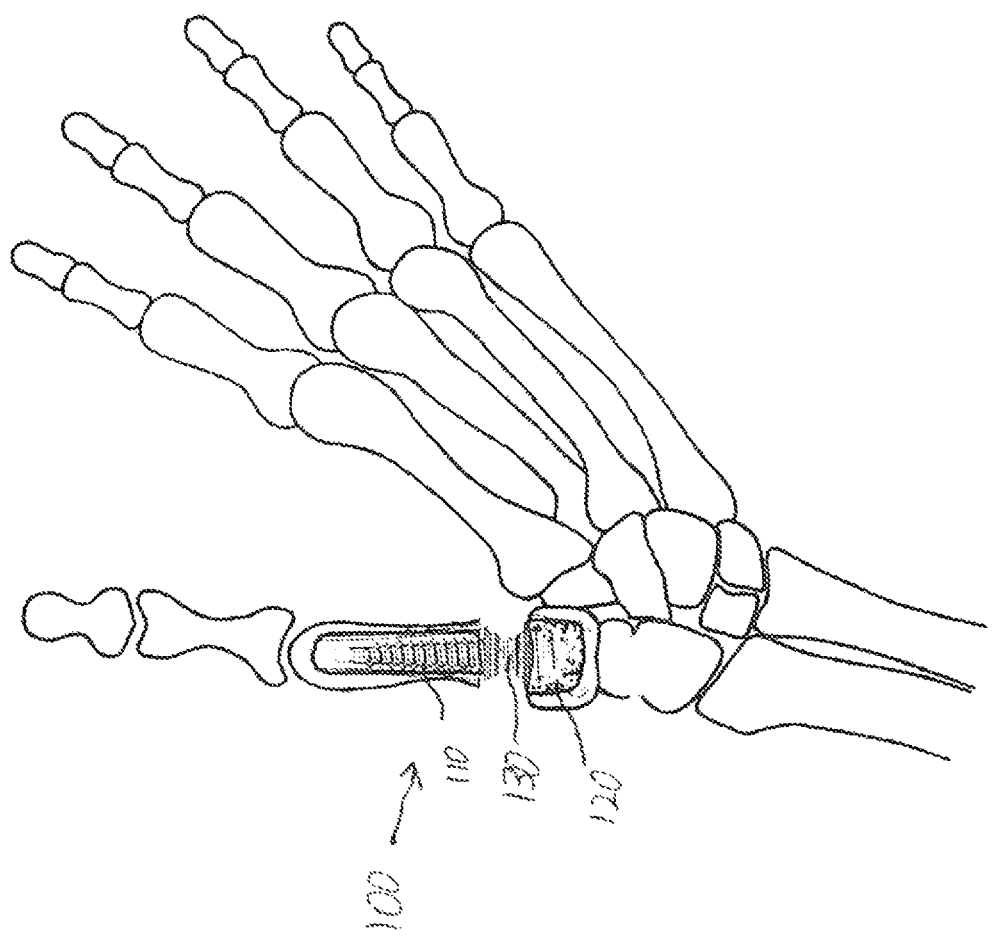
FIG. 9
FIG. 10A

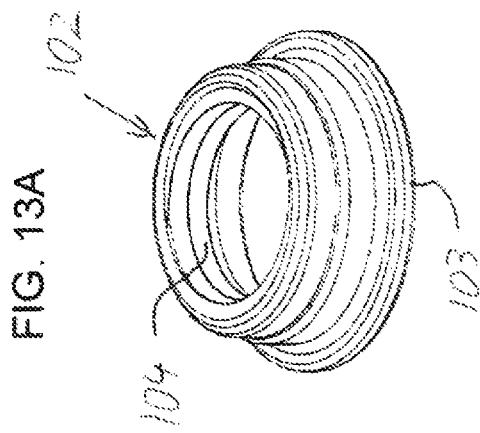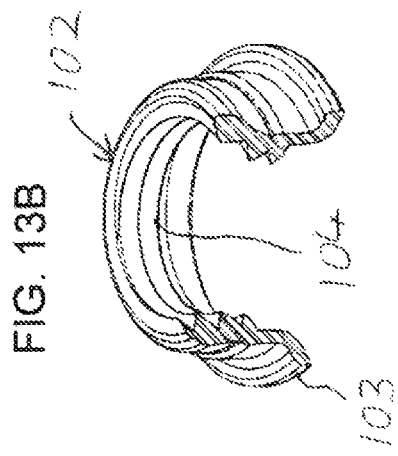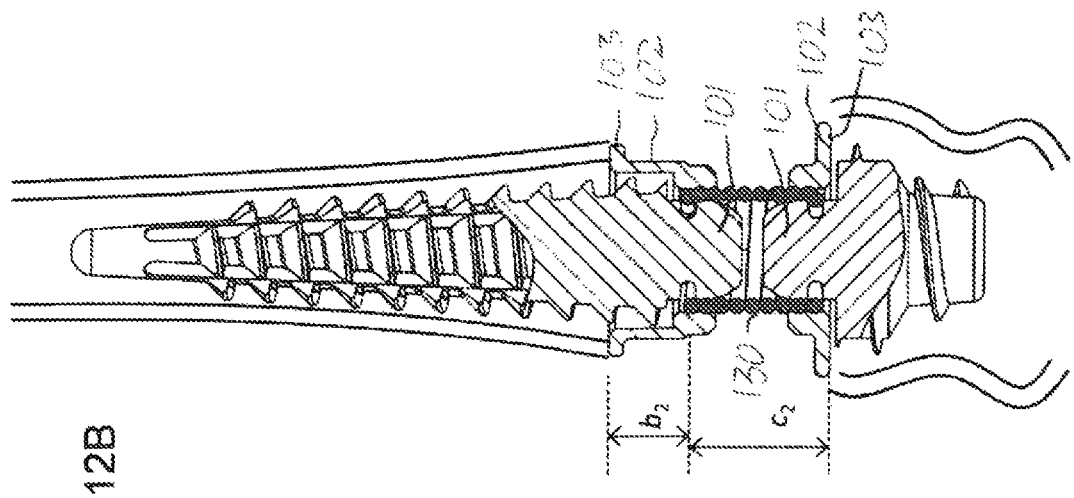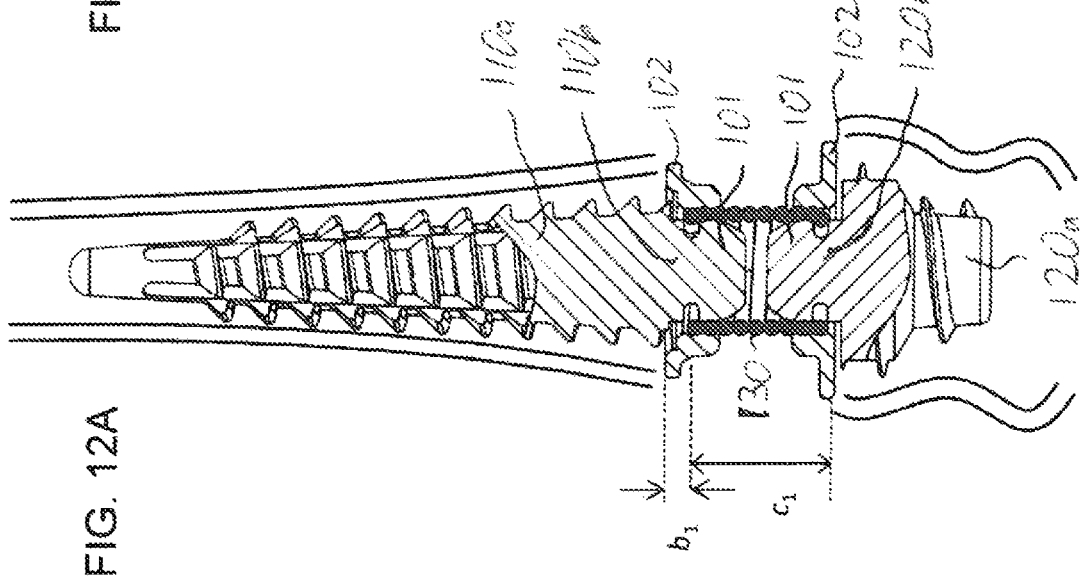

PROSTHESIS FOR REPLACING JOINT IN A HUMAN HAND OR FOOT

FIELD AND BACKGROUND OF THE INVENTION

The present invention relates to medical prostheses and, in particular, it concerns a prosthesis for replacing a joint between a first bone and a second bone in a human hand or foot.

The first elongated bone (metacarpal) at the base of the thumb is connected to the wrist trapezium through the carpometacarpal (CMC) joint which is sometimes referred to as the trapezio-metacarpal joint. This particular joint is of critical anatomical importance to humans, due to the opposing motion of the thumb with respect to the fingers for grasping objects and performing daily functions. Damage to the CMC joint through physical injury or disease can therefore be a severe physiological burden to inflicted humans.

Osteoarthritis, rheumatoid arthritis, and post-traumatic arthritis of the carpometacarpal (CMC) joint cause interminable pain and poor function of the thumb. Patients who have mild symptoms often respond to rest, immobilization, non-steroidal anti-inflammatory drugs, or intra-articular injections of steroids. However, patients who have more severe forms of trapezio-metacarpal (carpometacarpal) arthritis may have dorsoradial subluxation of the joint, adduction contracture of the first web space, severe loss of articular cartilage, secondary metacarpophalangeal hyperextension and interphalangeal flexion deformity accompanied with disabling pain and hand function weakness. Carpometacarpal arthritis is often an isolated entity, without significant concomitant involvement of the trapezio-scaphoid or trapezio-trapezoid joint. Moreover, retaining the trapezium in patients who have isolated trapezio-metacarpal arthritis is justified in order to preserve stability at the base of the thumb. Any carpometacarpal total joint replacement should restore the length and direction of the first metacarpal by reducing any existing subluxation of the metacarpal on the trapezium and by providing a fixed fulcrum for the metacarpal to articulate with the trapezium.

The goal of surgical intervention in patients who have CMC arthritis is to restore a strong, painless and stable thumb without deformity or decreased motion. Many reconstructive procedures have been devised including interposition arthroplasty, resection arthroplasty of the trapezium, resection interposition arthroplasty of the trapezium, and arthrodesis. Various types of prosthetic joints have been developed for surgical replacement of the metacarpophalangeal and interphalangeal joints of the fingers including the CMC joint of the thumb.

There have been a number of total CMC joint implants wherein implants described and marketed having articulating surfaces have been surgically inserted into both the base of the first metacarpal and the trapezium. Other alternatives include replacing the entire trapezium, either along with the base of the metacarpus or by itself.

Many of the proposed artificial joints employ sliding between the prosthesis parts or between the prosthesis and the joint tissues. The sliding movement is typically accompanied by wear and abrasion of the joint parts, which in turn leads to inflammatory reactions, bone absorption, loosening of the prosthesis and dislocations.

An alternative approach for a prosthetic joint is suggested by U.S. Pat. No. 6,342,076, which employs a number of spring elements extending from end-to-end of the joint. The use of springs avoids the issues caused by sliding motion, and provides various advantages. Springs, however, when unlimited, may allow excessive motion in undesirable modes of motion, such as lateral shear, and may pose a risk of collapse if subjected to axial loading while laterally deformed.

Reviews of evidence-based researches concluded that there are no significant differences between all reported surgical solutions and the classic trapeziectomy when end results were compared. But, simple total trapeziectomy (the gold standard treatment) does not fully restore the CMC joint function. There is a proximal migration of the first metacarpal, resulting in a decrease in key pinch, tip pinch and grasp power. Pain is typically decreased but not eliminated.

SUMMARY OF THE INVENTION

The present invention is a prosthesis for replacing a joint between a first bone and a second bone in a human hand or foot while preferably preserving the anatomical length of the joint member, maintaining joint stability and preserving an unlimited range of motion corresponding to the natural motion of the joint.

According to the teachings of an embodiment of the present invention there is provided, a prosthesis for replacing a joint between a first bone and a second bone in a human hand or foot, the prosthesis comprising: (a) a first rigid block comprising a bone anchor portion for fixation within the first bone and a first head portion to remain projecting from the first bone; (b) a second rigid block comprising a second head portion; (c) a flexible bridging structure comprising a helical spring deployed to bridge between the first head portion and the second head portion, the helical spring oriented such that a central axis of the helical spring is substantially aligned with a central axis of the bone anchor portion; and (d) at least one shear-limiting limiting element deployed within an internal volume of the helical spring so as to limit an extent of shear deformation applied to the helical spring.

According to a further feature of an embodiment of the present invention, the at least one shear-limiting element comprises a first rigid extension projecting from the first head portion along the inside of the helical spring and a second rigid extension projecting from the second head portion along the inside of the helical spring.

According to a further feature of an embodiment of the present invention, the first and second projections have convexly-curved lateral surfaces.

According to a further feature of an embodiment of the present invention, the first and second projections extend towards each other so as to together span a majority of an unsupported length of the helical spring between the first and second head portions.

According to a further feature of an embodiment of the present invention, the at least one shear-limiting element comprises a tether anchored to both the first head portion and the second head portion.

There is also provided according to the teachings of an embodiment of the present invention, a prosthesis for replacing a joint between a first bone and a second bone in a human hand or foot, the prosthesis comprising: (a) a first rigid block comprising a bone anchor portion for fixation within the first bone and a first head portion to remain projecting from the first bone; (b) a second rigid block comprising a second head portion; (c) a flexible bridging structure configured to bridge between the first head portion and the second head portion, the flexible bridging structure comprising a helical spring for attachment to the first head portion; and (d) a flange element including a flange, wherein the first head portion is configured for insertion into a first end of the helical spring, and wherein the flange element has a central bore for deployment around the helical spring, an outside surface of the first head portion and the central bore of the flange element being configured to lock the helical spring therebetween.

There is also provided according to the teachings of an embodiment of the present invention, a prosthesis for replacing a joint between a first bone and a second bone in a human hand or foot, the prosthesis comprising: (a) a first rigid block comprising a bone anchor portion for fixation within the first bone and a first head portion to remain projecting from the first bone; (b) a second rigid block comprising a second head portion; (c) a flexible bridging structure configured to bridge between the first head portion and the second head portion; and (d) a flange element including a flange, wherein the flange element is configured to be displaceable relative to the bone anchor so that, after fixation of the bone anchor within the first bone; the flange is displaced until the flange comes into contact with the first bone, thereby distributing forces transferred through the prosthesis over a contact surface of the flange against the first bone.

According to a further feature of an embodiment of the present invention, the central bore has a helical groove configured for engaging an outside surface of cods of the helical spring, the flange element being displaceable relative to the bone anchor by threaded motion along the helical spring.

According to a further feature of an embodiment of the present invention, an outside surface of the first head portion and the central bore of the flange element are configured to lock the helical spring therebetween.

According to a further feature of an embodiment of the present invention, an outside surface of the first head portion has a peripheral recess for receiving at least an end coil of the helical spring, and wherein the central bore of the flange element is configured to trap the end coil of the helical spring within the recess.

According to a further feature of an embodiment of the present invention, the flange element is configured to be displaceable relative to the bone anchor so that, after fixation of the bone anchor within the first bone, the flange is displaced until the flange comes into contact with the first bone, thereby distributing forces transferred through the prosthesis over a contact surface of the flange against the first bone.

According to a further feature of an embodiment of the present invention, the flange element is one of a set of at least two flange elements usable interchangeably to engage the outer surface of the coils of the helical spring, the at least two flange elements differing from each other in an axial distance from the flange to an end of the central bore.

There is also provided according to the teachings of an embodiment of the present invention, a prosthesis for replacing a joint between a first bone and a second bone in a human hand or foot the prosthesis comprising: (a) a first rigid block comprising a bone anchor portion for fixation within the first bone and a first head portion to remain projecting from the first bone; (b) a second rigid block comprising a second head portion; (c) a flexible bridging structure configured to bridge between the first head portion and the second bead portion, wherein the flexible bridging structure comprises a leaf spring having a length, the leaf spring being preformed with a helical twist that turns through at least 90 degrees along the length of the leaf spring.

According to a further feature of an embodiment of the present invention, the second rigid block further comprises a bone anchor portion for fixation within the second bone.

According to a further feature of an embodiment of the present invention, the prosthesis is configured for forming a joint between a first metacarpal and a trapezium.

According to a further feature of an embodiment of the present invention, the second rigid block is an intermediate block of the prosthesis, the prosthesis further comprising: (a) a third rigid block comprising a bone anchor portion for fixation within the second bone and a third head portion to remain projecting from the second bone: and (b) a second flexible bridging structure configured to bridge between the second rigid block and the third rigid block.

According to a further feature of an embodiment of the present invention, the prosthesis is configured for forming a joint between a first metacarpal and a scaphoid after removal of a trapezium.

According to a further feature of an embodiment of the present invention, the second block is configured for rigid anchoring to a trapezoid.

There is also provided according to the teachings of an embodiment of the present invention, a method for forming a joint in the human hand after removal of a trapezium, the method comprising the steps of: (a) rigidly anchoring a first block to a first metacarpal; (b) rigidly anchoring a second block to a trapezoid; (c) rigidly anchoring a third block to a scaphoid; (d) providing a flexible bridging structure between the first block and the second block so as to form a first joint; and (e) providing a flexible bridging structure between the second block and the third block so as to form a second joint.

BRIEF DESCRIPTION OF THE DRAWINGS

The invention is herein described, by way of example only, with reference to the accompanying drawings, wherein:

FIG. 1A is a schematic skeletal view of a human hand illustrating deployment of a prosthesis according to the teachings of an embodiment of the present invention for replacing a joint between a first metacarpal and a trapezium in a human hand;

FIG. 1B is an enlarged view of a region of FIG. 1A showing the prosthesis of FIG. 1A in more detail:

FIG. 2A is a side view of the prosthesis of FIG. 1A;

FIG. 2B is a cross-sectional view taken along the line X-X of FIG. 2A;

FIG. 2C is an enlarged view of a region of FIG. 2B;

FIG. 3A is a view similar to FIG. 2B showing the prosthesis undergoing lateral flexion;

FIG. 3B is a view similar to FIG. 2B showing the prosthesis undergoing lateral shear deformation:

FIG. 4 is a partial view similar to FIG. 2B illustrating a first alternative configuration for anchoring an internal tether of the prosthesis;

FIG. 5 is a partial view similar to FIG. 2B illustrating a second alternative configuration for anchoring an internal tether of the prosthesis;

FIGS. 6A and 6B are side views of an alternative embodiment of a prosthesis for replacing a joint between a first bone and a second bone in a human hand or foot, the prosthesis being shown in a straight and a deflected state, respectively;

FIGS. 7A and 7B are views similar to FIGS. 6A and 6B, respectively, illustrating a variant implementation of the prosthesis employing bone-contact flanges;

FIG. 8 is a side view similar to FIG. 2A illustrating the prosthesis with additional alignment markings;

FIG. 8A is a side view of a jig for use with a prosthesis having markings such as those of FIG. 8 to provide properly aligned drilling holes for lateral bone screws;

FIG. 9 is a schematic skeletal view of a human hand illustrating deployment of a prosthesis according to the teachings of an alternative embodiment of the present invention for replacing a joint between a first metacarpal and a trapezium in a human hand;

FIG. 10A is an enlarged view of a region of FIG. 9 showing the prosthesis of FIG. 9 in more detail;

FIGS. 12A and 12B are views similar to FIG. 10B illustrating deployment of the prosthesis using flanges of different axial dimensions;

FIGS. 13A and 13B are isometric views of a selected flange from a set of flanges of differing axial dimensions, shown in full and cut-away views, respectively;

DESCRIPTION OF THE PREFERRED EMBODIMENTS

Figures 6C, 6D:
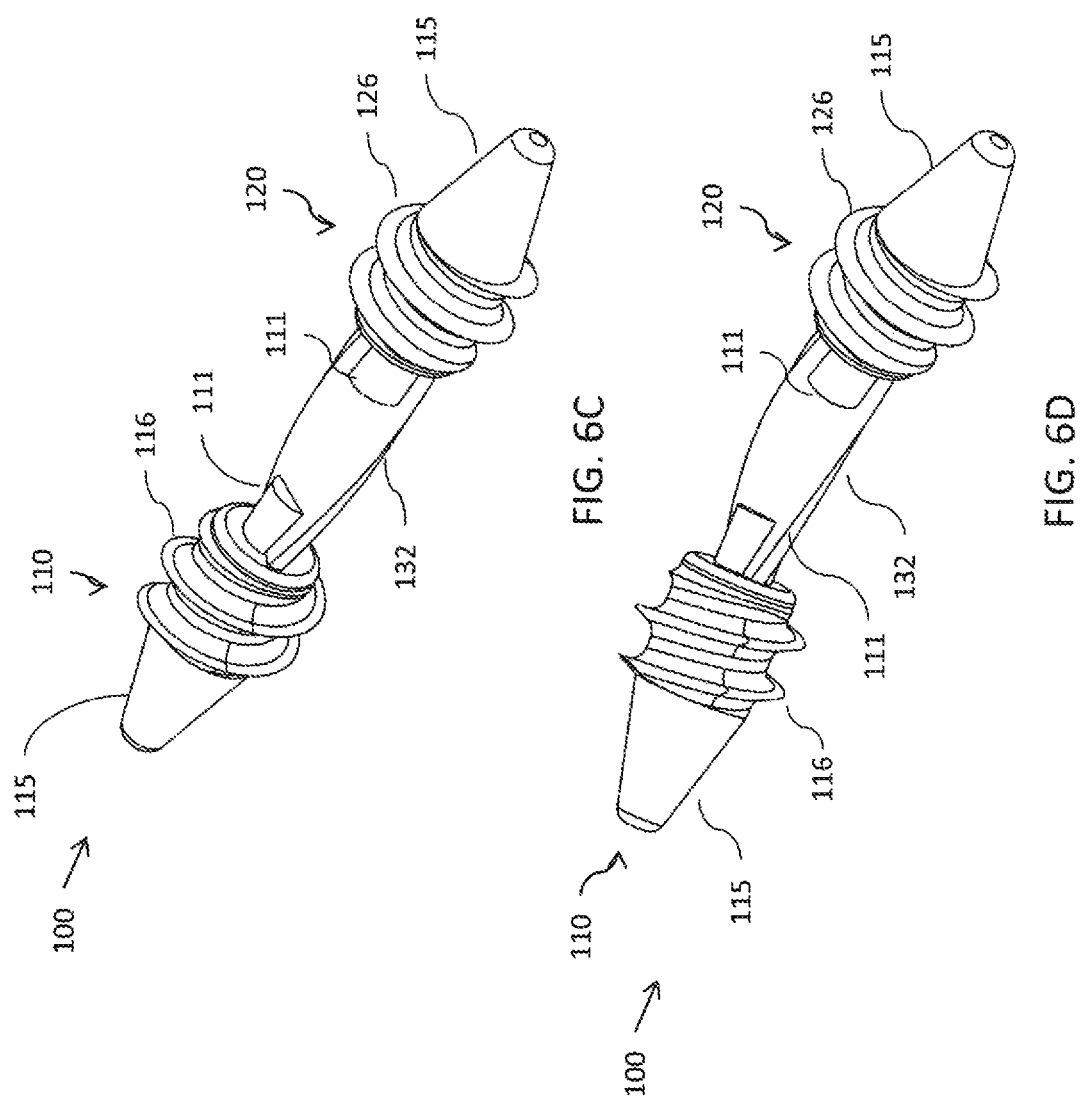
FIGS. 6C and 6D are isometric views of the prosthesis of FIGS. 6A and 6B shown in a straight and a deflected state, respectively.

The present invention is a prosthesis for replacing a joint between a first bone and a second bone in a human hand or foot.

The principles and operation of prostheses according to the present invention may be better understood with reference to the drawings and the accompanying description.

By way of introduction, it should be noted that the present invention encompasses a number of aspects, each with a number of different implementation options, which are considered to be of patentable significance, and which may be used together to particular advantage in various combinations. Specifically, a first aspect of the invention relates to various implementations of a prosthetic joint employing a helical spring, where certain modes of motion of the spring are limited by elements deployed within the spring. A second aspect of the invention relates to a tightenable bone-contact flange for use as part of the prostheses of the present invention. A third aspect of the present invention relates to a twisted-leaf-spring implementation of a flexible bridging structure of the prosthesis. These and other aspects of the present invention will each be addressed in detail below with reference to the drawings.

Helical Spring with Motion Limiter

Turning now to a first aspect of the invention, this relates to a prosthesis for replacing a joint between a first bone and a second bone in a human hand or foot. By way of one particularly preferred but non-limiting example of the invention, the invention will be illustrated in the context of a replacement CMC joint, where the first bone is the first metacarpal and the second bone is the trapezium or, in other cases referred to below where the trapezium is completely removed, the second bone is the scaphoid.

Using terminology and numbering which refer generically to all implementations of the invention except where specified otherwise, the prosthesis (100) has a first rigid block (110) including a bone anchor portion (110a) for fixation within the first bone and a first head portion (110b) that remains projecting from the first bone. A second rigid block (120) has a second head portion (120b), and in this case also a bone anchor portion (120a) for fixation within the second bone. A flexible bridging structure includes a helical spring (130) deployed to bridge between first head portion (110b) and second bead portion (120b). Helical spring (130) is oriented such that a central axis of the spring is substantially aligned with a central axis of the bone anchor portion. It is a particular feature of this aspect of the present invention that the prosthesis also includes at least one shear-limiting element deployed within an internal volume of helical spring (130) so as to limit an extent of shear deformation applied to the helical spring.

Before addressing the features of the various embodiments of the present invention in more detail, it will be helpful to define certain terminology as used herein in the description and claims. Firstly, as already mentioned, various embodiments of the present invention employ a helical spring as the flexible bridging element between two rigid blocks of the prosthesis. The term "helical spring" is used herein in the description and claims to refer to any spring element in which a majority of its effective length is formed by one or more elongated element that forms a sequence of coils that sit one-on-the-next in its most shortened state, and which can be stretched or undergo flexion. The "helical spring" of embodiments of the present invention may thus vary considerably from a perfect cylindrical helix, and may include variations in coil diameter, in filament thickness or cross-sectional shape, along the length of the spring. Furthermore, the spring element may optionally be modified to allow interconnection or integration with some other element at an intermediate position along a length of the spring, and/or may be modified at its extremities to facilitate attachment to the rigid blocks of the present invention. In a subset of particularly preferred implementations, a cylindrical spring of constant diameter and constant filament cross-section is used. According to certain particularly preferred implementations, the helical spring is a "normally closed" spring, i.e., where adjacent coils are closed against each other in the absence of an applied load. According to alternative preferred implementations, part or all of the spring may have a normally-open configuration, where the coils are initially somewhat spaced apart, and can be closed together under application of axial compression of above some threshold value, where the threshold is preferably an amount smaller than 500N.

Reference is made herein to a central axis of the spring. To the extent that the undeformed state of the spring is cylindrical or otherwise axisymmetric, the central axis of the spring is taken to be the central axis in its simple geometrical sense. To the extent that the spring varies somewhat from an axisymmetric form, the central axis is defined intuitively as the general direction of extension along which the coils of the spring progress. If there is any curvature to the direction of extension thus defined, an average direction is used as the "central axis".

Where reference is made to a "central axis" of a bone anchor portion, this refers to the central axis of any elongated portion which is inserted into a channel within the bone, and typically corresponds to the direction of insertion of the bone anchor. In the case of insertion into a bone with a direction of elongation, this most preferably also corresponds during use with the direction of elongation of the bone, signifying that the anchor is typically inserted along a central channel within the bone.

Where reference is made to the central axis of the spring being "substantially aligned" aligned with the central axis of a bone anchor, this refers to an orientation of the spring in which axial compression in a direction along the bone anchor axis and/or along the direction of elongation of the bone results in compression force that presses together the coils of the helical spring. This functional definition is intended primarily to differentiate thus-defined implementations from devices where springs are deployed crossways to the hone insertion direction, and does not require precise alignment. Deviations of as much as 20-30 degrees may be considered "substantially aligned" according to this definition, and deviations of up to 10 degrees may be considered "aligned" for the purpose of this definition.

Motion Limiter—First Embodiment

Turning now to details of the "shear-limiting element", according to a first subset of implementations of this aspect of the present invention illustrated herein with reference to FIGS. 2A-5, the at least one shear-limiting element is implemented as a tether (140) anchored to both first and second blocks (110, 120). The tether is preferably implemented as a flexible but substantially non-stretching cable, further detailed below. The tether is preferably without tension in the neutral position of FIGS. 2A-2C, in which the coils of spring (130) are preferably closed. The length is preferably chosen such that, during lateral flexion as shown in FIG. 3A, as the coils move apart on one side of spring (130), tether (140) is gradually pulled tight, taking the shortest path through the inside of spring (130), and reaches a limit only at the design limit of flexion of the joint, which depends upon the joint but may be, for example, around 15 degrees.

Tether (140) is particularly effective at limiting shear motion, such as is illustrated in FIG. 3B, where blocks (110, 120) start to undergo relative motion laterally without angular flexion. Such a motion is accompanied by formation of a "S-bend" curvature in spring (130) in which coils become separated on opposite sides of spring (130) at different regions along its length, leading both to an increase in the vertical height with lateral motion and tending to extend the path of tether according to the hypotenuse of a triangle formed by the height and the lateral displacement. As a result, tether (140) is effective to arrest such lateral shear motion after a small displacement, thereby preventing further deflection of the spring and maintaining stability of the overall structure under a wide range of stress conditions.

As already mentioned, a preferred embodiment of the invention as illustrated in FIG. 1 is an implant device (100) intended to replace of a joint of the human body, and specifically in this example, to replace the carpometacarpal (CMC) joint at the base of the human thumb. The implant device (100) is in the form of a prosthesis composed of three elements or members. The first rigid block (110) serves as an anchoring bit to be implanted within the first metacarpal hone of the thumb. The other rigid block (120) serves as an anchoring bit to be implanted within the trapezium of the wrist. The flexible bridging element (130) bridges between the two rigid blocks (110 and 120). When a tendon pulls one of the connected bones adjacent to the joint, the flexible bridging element (130) is deflected accordingly and allows the bone to perform its desired motion.

The flexible bridging element is designed to provide enough strength to hold the bones on two sides of the joint in the correct place. In this action the flexible bridging element (130) mimics the action of the ligament tissue that surrounds a normally functioning joint. On the other hand flexible bridging element (130) is sufficiently flexible to allow the tendon to pull the bones to the desired position without much effort. In the case of the CMC joint, these properties combine to provide a relatively large range of motion and an improved pinch strength.

Because the motion of the joint is achieved without friction between sliding surfaces, there are typically minimal wearing effects. Wearing effects of joints are associated with inflammatory reactions (worsening of the Osteoarthritis situation) with reduced range of motion and decreased pinch strength.

In certain preferred embodiments, the replacement joint is provided without causing functional damage to surroundings bones and joints because the implant is anchored only to the bones of the joint (In this example, the first metacarpal hone of the thumb and the trapezium) without using other surrounding bones (for example the trapezoid) or tendons for anchoring.

In this and other examples of the present invention that employ a helical spring as an elastic member, the helical spring exhibits certain advantages over a leaf spring (cantilever elastic beam): it has low stiffness for deflection but high resistance to buckling. As a result, on one hand, the helical spring (130) can withstand relatively high axial compression force and, on the other hand, it is easily flexed by applying relatively low moments.

As illustrated in FIG. 3A when deflecting the helical spring (130) the deflection is divided equally between active turns. The small deflections (on each turn) create sheer stresses that are also distributed almost equally over the active turns. Hence a large deflection (bending) of the helical spring expressed in low uniform stress. High concentrated stresses are major factor for fatigue failures of mechanical structures. Therefore helical spring has more fatigue strength than a beam which means it can withstand more operating cycles.

The helical spring (130) is preferably made of high elasticity materials such as but not limited to stainless steel AISI 302.

It worth noting that in some replacement joints of the prior art there are portions of the prosthesis that are likely to develop concentrated stress which in turn might lead to fatigue failure.

The helical spring (130) as illustrated here in this non-limiting example is mounted on a threaded protrusion (111) which serves as the head portion of the anchoring bits (110 and 120). The helical spring (130) is fastened to the protrusion (111) by the thread, or by any other suitable anchoring configuration. In this case, the coils of the spring act as threading, tightening into engagement with threaded protrusion (111) like a threaded nut. The spring could also be fastened by welding, soldering, etc.

As mentioned above, according to the example illustrated in FIGS. 2A-3B, the extension of the helical spring is limited by tether (140), referred to also as an "internal wire". The internal wire (140) is preferably a threaded wire—a structure that provide high strength for tension loads and great flexibility for bending. The internal wire (140) is preferably made of high elasticity materials such as but not limited to stainless steel ASME 302 and Super Elastic Nitinol. In order to ensure high tensile strength in combination with high flexibility, certain particularly preferred implementations of the invention employ a multi-strand metal cable for tether (140).

The internal wire (140) may advantageously be fastened to the anchoring bits (110 and 120) by a loop (141). The internal wire (140) runs through hole (112) form a loop (141) and return to the hole (112). Because the Loop is too wide to pass through the hole (112) it lock the wire (140) to the anchoring bit (110 or 120). The Loop (141) can be formed by soldering (113), welding, adhesives, etc.

In another example of prefer embodiment illustrated in FIG. 4 the internal wire (140) is fastened to the anchoring blocks (110, 120) by clamping screw (114). It worth noting that fastening of wire (140) to a block (110 or 120) may be implemented using many other conventional techniques such as but not limited to welding, soldering adhering etc.

Limiting the extension of the helical spring (130) as described above secures the parts of the joint (100) together and provides limits to its range of motion. In this form the suggested artificial joint (100) mimics the action of the ligament tissue in a normal joint.

In preferred embodiment, the first and second bone-anchoring portions are of generally cone shape such that it could be introduced by pushing into the spongy part of the bone. For example the first and second anchoring bits (120 and 110) that are illustrated in FIGS. 2A-5 have a generally conical tip (115) that allows it to be introduced into the first metacarpal bone of the thumb and into the trapezium (in this example) by pushing the cone tip (115) into the Trabecular (spongy) part of the bone.

And in another example of prefer embodiment illustrated in FIG. 5 the internal wire (140) is fastened to the anchoring bits (110, 120) by loop (141). The internal wire (140) runs through hole (112) in bushing (118). Then it forms a loop (141) and then returns to the hole (112). This approach is similar to the example in FIG. 2C, but in this example, the loop is secured within the blind hole (112b) at the bottom of the internal thread 119. In this arrangement there is no need to use additional process such as welding, soldering, adhering, etc. to secure the loop. In this example the cone shape could be of sharp shape because there is no axial hole that runs through the cone as in the examples illustrated in FIGS. 2A-4.

As illustrated in FIG. 2 the first and second anchoring bits (110, 120) elements are having protruded self-tapping like thread (116) that allows securely anchoring the element to the Trabecular (spongy) part of the bone. In addition the bits (110, 120) preferably have lateral through holes (117) that are used to fasten the bit to the bone by use of standard orthopedic locking screws (151, 152 shown in FIG. 1B).

In certain preferred embodiments, portions of the surfaces of the first and second anchoring elements are coated with biocompatible metallic porous coating, for example, as described in U.S. Pat. No. 3,605,123. This coating provides enhanced bone fixation. The particles composed the porous coating layer may be deposited by any one of a number of well-known processes including but not limited to a flame-plasma process, in which several parameters are controlled as functions of the size of the particles.

For example the outer surfaces of anchoring bits (110, 120) illustrated in FIGS. 2A-5 may be coated in such a way.

Motion Limiter—Second Embodiment

Turning now to a further embodiment illustrated with reference to FIGS. 9-15, in this case, the at least one shear-limiting element is implemented as a first rigid extension projecting from first head portion (110b) along the inside of helical spring (130) and a second rigid extension projecting from second head portion (120b) along the inside of helical spring (130). These rigid projections, labeled (101), are best seen in the enlarged cut-away view of FIG. 10C. Projections (101) preferably have convexly-curved lateral surfaces, and preferably extend towards each other so as to together span a majority of an unsupported length of helical spring (130) between first and second head portions (110b, 120b). The "unsupported length" of spring (130) is the portion of the spring which is free to take part in motion of the joint prosthesis and, in this case, corresponds to the space between the regions caught between the head portions and the inner bores of flange elements, described further below. In the case illustrated in FIG. 10C, projections (101) project distances $d_1$ and $d_2$, respectively, from first and second head portions (110b, 120b), and a remaining space between the projections in the neutral state of the joint is a. Since $d_1+d_2>a$, this configuration satisfies the aforementioned preferred condition that the projections together span a majority of the unsupported length of the helical spring.

Figure 11A:
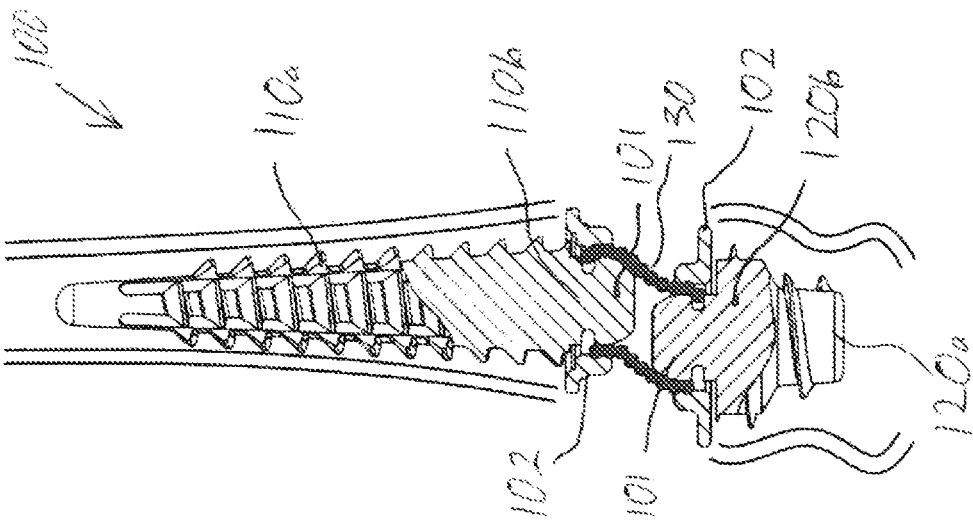
FIG. 11A is a view similar to FIG. 10A showing the prosthesis undergoing lateral flexion.
Figure 11B:
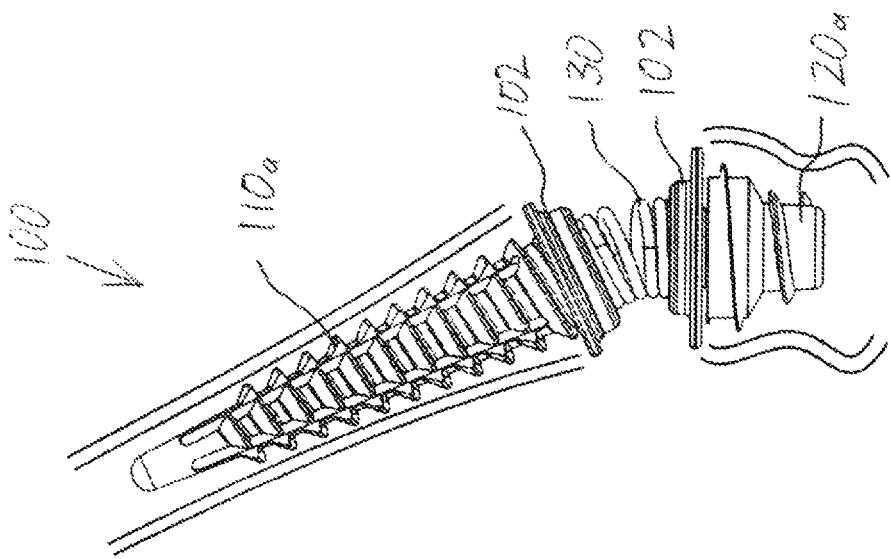
FIG. 11B is a view similar to FIG. 10B showing the prosthesis undergoing lateral shear deformation.

The significance of projections (101) will be best understood with reference to FIG. 11B which shows a partially cut-away view of the prosthesis during application of lateral shear forces. The presence of projections (101) limits the extent to which lateral deflection of helical spring (130) can occur. Specifically, where convex lateral surfaces are provided, as the spring starts to deflect laterally, progressively more coils of the spring come into contact with the surface of projections (101), thereby immobilizing those coils so that no further deflection of those coils can occur, and so that the free length of the spring progressively shortens. The projections thus effectively delimit a maximum lateral (shear) deflection within bounds that maintain stability and structural integrity of the spring.

As mentioned earlier, the spring may be either of a normally-closed or a normally-open coil configuration. Here and in all helical-spring embodiments of the present invention, the spring is advantageously implemented with proportions which tend to enhance stability of the spring under axial loading. Particularly preferred implementations use an unsupported length of the spring which is no more than twice the diameter of the helical spring, and most preferably no more than about 1.4 times the diameter of the helical spring.

Displaceable Flange Configurations

Turning now to a further aspect of the present invention, it is of particular value that loads transferred through prosthesis (100) are transferred to the strong cortical bone of the adjacent bones, and not to the softer inner cancellous bone. Anchoring of the prosthesis to the cortical bone may be achieved either through the use of transverse locking screws that pass transversely through the bone anchor portion and through the layers of cortical bone, as illustrated in FIGS. 1A and 1B, or by use of a flange which distributes loads over a sufficient area of the surface of the bone adjacent to the joint to reach the cortical periphery. Certain further aspects of the present invention relate to particular configurations and additional functionality related to prostheses employing flanges.

Thus, in the embodiments of FIGS. 7A-7B and 9-15, each rigid block provided with a bone anchor portion is also provided with a flange element (102) including a flange (103). Flange element (102) is configured to be displaceable relative to the respective bone anchor so that, after fixation of the bone anchor within the bone, flange (103) is displaced until it comes into contact with the bone, thereby distributing forces transferred through the prosthesis over a contact surface of the flange against the first bone. The ability of flange element (102) to be displaced relative to the bone anchor portion is valuable in that it allows the bone anchor portion to be well seated in the bone before the flange is deployed against the bone tissue, thereby facilitating intimate contact of both the bone anchor and the flange with the bone tissue. In certain particularly preferred implementations, the flange element provides various additional, or alternative, advantageous structures and functions, which will now be detailed.

A further set of preferred features of the flange element (102) relate specifically to embodiments in which the flexible bridging element is a helical spring, as in FIGS. 9-15. In this case, first head portion (110b) is configured for insertion into a first end of helical spring (130), and flange element (102) has a central bore (104) for deployment around helical spring (130). The outside surface of first head portion (110b) and central bore (104) of flange element (102) are advantageously configured to lock the helical spring therebetween.

According to certain particularly preferred implementations, central bore (104) has a helical groove, best seen in FIGS. 13A and 13B, configured for engaging an outside surface of coils of helical spring (130). Flange element (102) is thus displaceable relative to bone anchor portion (110a) by threaded motion along helical spring (130), i.e., as if helical spring (130) were a bolt on which flange element (102) is engaged. The helical groove may have a groove shape conforming to at least part of the external surface of the helical spring, or may be implemented as a conventional screw-thread cross-section, or any other desired cross-sectional shape.

Figure 10B:
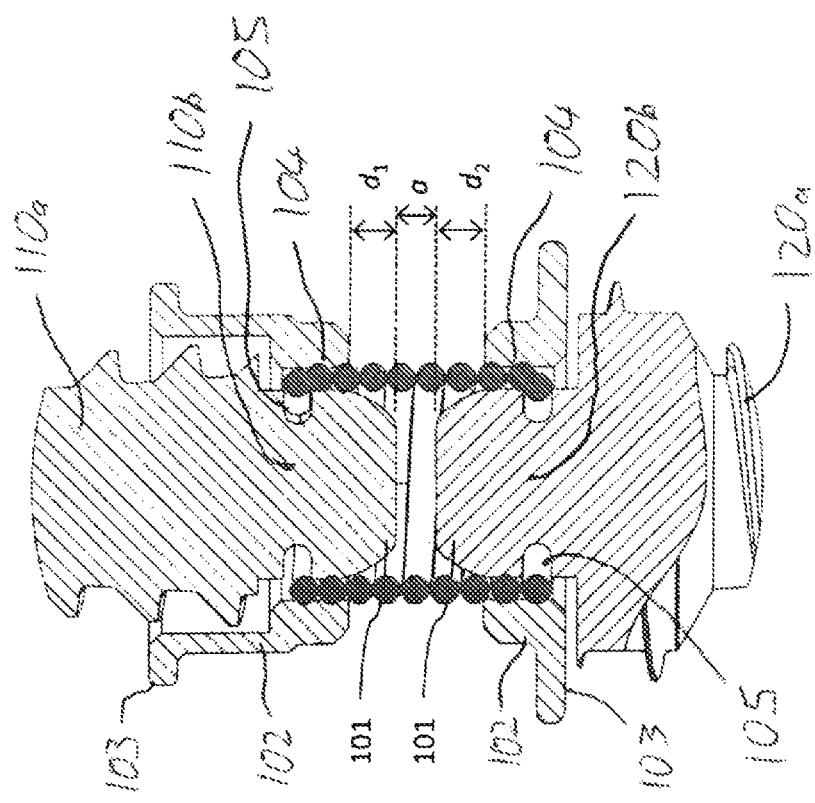
FIG. 10B is a partially cut-away view of the prosthesis of FIG. 10A.
Figure 10C:
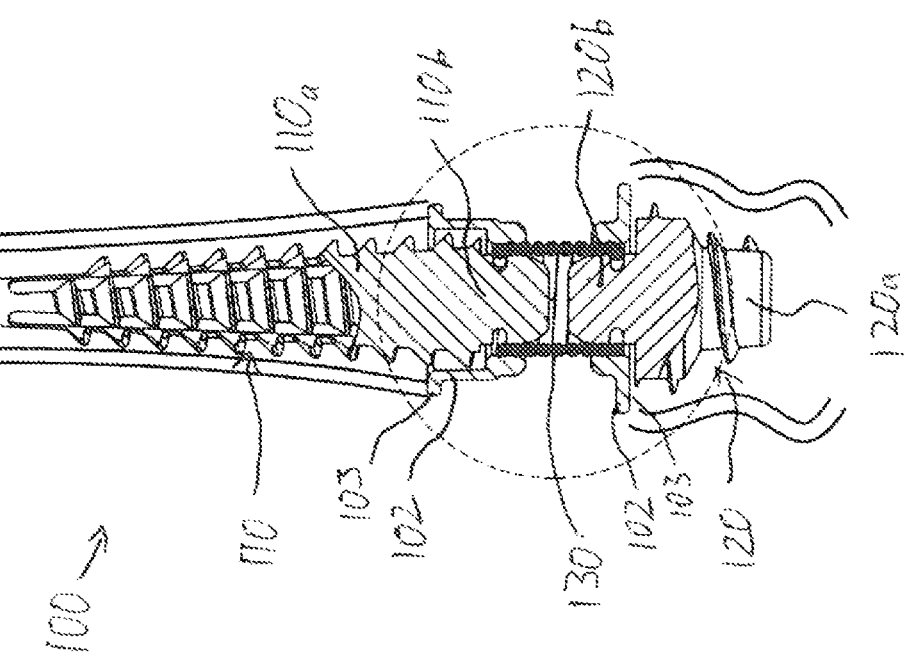
FIG. 10C is an enlarged view of a region of FIG. 10B.

According to a further feature of certain particularly preferred implementations, an outside surface of first head portion (110b) has a peripheral recess (105), best seen in FIG. 10C, for receiving at least an end coil of helical spring (130). Specifically, head portion (110b) is here preferably formed with a slight outward conical angle which slightly stretches the diameter of the coils of helical spring (130) as they are forced over the head portion during assembly, and at least the end coil reverts to its relaxed diameter when it encounters recess (105), providing a snap-lock-engagement of helical spring (130) onto head portion (110b). When flange element (102) is subsequently advanced according to its threaded motion to a position overlapping recess (105), it is effective to trap the end coil of helical spring (130) within recess (105). Specifically, in order to retract over head portion (110b), the end coil would need to expand outwards and seat itself neatly into the helical groove on the inside surface of central bore (104). However, axial forces are ineffective to generate such a radial outward displacement, resulting in a highly effective locking effect which abrogates the need for welding or other fixing techniques.

A further issue that is preferably addressed by the flange features of the present invention relates to adjustability in view of differing amounts of bone that are removed by a surgeon. During a surgical procedure for inserting a prosthetic joint, all structurally compromised tissue from the joint and adjacent bones is first removed. The surgeon frequently makes a judgment call during the procedure itself as to how much tissue should be removed, since the exact extent of tissue damage around the joint may not be evident from non-invasive imaging modalities. As a result, the surgeon is often left with conflicting requirements: on one hand, to reconstruct and maintain the original physiological structure of the bone structure, and most critically, the original length of the thumb or finger; on the other, the need to ensure that load bearing surfaces of the implanted bone anchor properly seat themselves against the bone surface, and particularly, the cortical outer layer of the bone.

According to a further aspect of the present invention, this issue is addressed by providing a set of at least two, and typically 3-6, flange elements (102) usable interchangeably to engage the outer surface of the coils of the helical spring. The different flange elements differ from each other in an axial distance from flange (103) to the nearer an end of central bore (104). An example illustrating the use of two different flange elements (102) of different axial dimensions is illustrated in FIGS. 12A and 12B, where FIG. 12A illustrates a case where relatively little bone was sectioned, and a short flange element (102) is used to provide abutment to the remaining bone covering a gap $b_1$. FIG. 12B illustrates a case of similar joint geometry, and with a similar overall length of the thumb, but where a larger proportion of the distal bone was cut away during the preparatory procedure. In this case, use of a flange element (102) with a longer axial dimension compensates for a larger gap $b_2$ and ensures that intimate bone contact and effective transfer of load to the cortical bone are still achieved. In both cases, the dimensions of the flexion region of the prosthetic joint $c_1=c_2$ are maintained the same, and the overall length of the thumb is preserved.

As illustrated in FIGS. 9-12B, the replacement joint (100) is here equipped with two adjustable flanges. During the implementation procedure, each side of the replacement joint is seated into the bone, by use of a self-tapping bone anchoring configuration and/or with locking screws, at the desired position, so as to ensure that the overall natural length of the finger/thumb will be preserved. Then, the location of the flange is adjusted to close the flange surface against the tissue, thereby distributing forces to the cortical exterior of the bone and/or clamping the end of the helical spring and defining the extent of the unsupported portion of the spring which takes part in flexion of the joint.

As a result, the desired anatomy of the joint is maintained, including the length of the thumb in this example of the CMC joint. In addition the flange prevents application of localized pressure in the contact area between the locking screw and the bone.

The CMC replacement joint thus preferably serves as an adjustable spacer that maintains a fixed predetermined gap between the Trapezium and the metacarpal bone base and thus keeps the original length of the thumb. This predetermined length is well preserved with minimal deterioration over time.

Arthritic changes reduces the effective contact surfaces of the CMC joint, consequently increasing the concentrated pressure on the joint and accelerating the further damages to the joint cartilage. The use of two adjustable flanges, or interchangeable flanges chosen to be of the required length dimension, helps to reduce any localized application of pressure by enlarging the contact surfaces of the joint. The arthritic changes in the CMC joint occur according to some theories due to gradually increased articular ligament loosening which renders the joint unstable. Instability causes the creation of concentrated forces and pressures unevenly distributed on the articular cartilage result in excessive attrition and cartilage abrasion. The CMC replacement joint provided by embodiments of the present invention maintains metacarpus-trapezium stability while allowing the necessary degree of metacarpus free motion with no need to reconstruct any ligament.

Leaf Spring Implementations

In another embodiment of the present invention illustrated in FIGS. 6A-7B, the flexible bridging structure is implemented as a leaf spring (132), preformed with a helical twist that turns through at least 90 degrees along a length of the leaf spring. The leaf spring (132) is twisted about its length by at least about 90° such that it allows deflection in any lateral direction. Specifically, as a result of the helical twist, for any given direction of lateral deflection, at least some portion of the leaf spring faces with its smallest dimension in the required flexion direction so as to facilitate the required flexion. The spring beam (132) is fastened to the protrusion (111) by welding, soldering, adhering, etc. The spring beam (130) is preferably made of high elasticity materials suitable for implementation such as but not limited to stainless steel AISI 316L or AISI 316LVM comply with ASTM F138.

In this example the rigid blocks (110, 120) have self-tapping bone-anchor portions (116 and 126) that securely anchor the element to the Trabecular (spongy) part of the bone. According to one implementation option, threads (116, 126) are opposite one to each other such that by turning the implant in one direction (say counter clockwise) the threads on both anchoring bits (110, 120) screw into the bones and on each side fasten it to the joint.

This structure is typically more robust then the joint presented in FIG. 2 as the implant is a single body such that there is typically no need for additional parts to limit its range of motions.

In this embodiment (FIGS. 6A-7B) the anchoring bits (110, 120) could also coated with biocompatible metallic porous coating as discussed above. The example of FIGS. 7A-7B is similar to that of FIGS. 6A-6D, but additionally features adjustable flanges (102), with structure and functionality as discussed above. In this case, the flanges do not serve a locking function in relation to the flexible bridging structure, and can therefore be adjusted along the length of a relatively long range of adjustment, typically along a dedicated threaded neck portion of the first and second rigid blocks, without requiring a set of different sized flanges.

Alignment Jig

In an example of a preferred embodiment illustrated in FIG. 8, the flexible bridging element (130) is marked with longitudinal (133) and circumferential (134) crossed marks. Those marks (133 and 134) assist the surgeon to introduce the locking screw (151 and 152 shown in FIG. 1) through the bone to the right location within the locking hole (117). The surgeon can be assisted with jig or template (200) illustrated in FIG. 8A. The jig (200) has a longitudinal (233) and crossed lateral (234) slots. When the marks (133 and 134) of the replacement joint (100) appear within the slots the locking holes (117) are in correct position against the location holes (217) of the jig (200) so that the surgeon can drill through the holes (217) into the bone and then introduce the locking screws (151 and 152) to the locking holes.

The human CMC Joint (CMCJ) is a Saddle type joint providing stability together with greater flexibility than a hinge or gliding joint. The mobile metacarpus bone which sits on the saddle is able to move in an oval shape motion relative to the trapezium by a rolling type of motion that should prevent cartilage abrasion. The replacement joints according to certain embodiments described herein mimic this saddle joint feature by using a flexible helical spring linking the joint components (MC-Trapezium) and enables rolling motion with no friction and abrasion of its components.

The above mentioned flexible helical spring restores the CMCJ kinematics and simply determines the metacarpal bone movements by its unique design.

Implementations Where Trapezium is Removed

Figure 15:
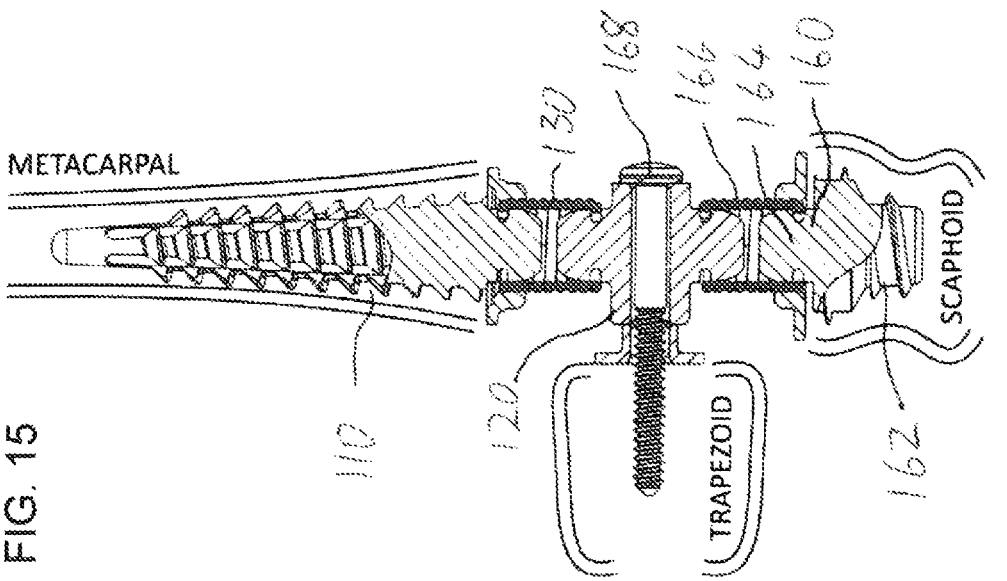
FIG. 15 is an enlarged view of a region of FIG. 14 showing the prosthesis of FIG. 14 in more detail.
Figure 14:
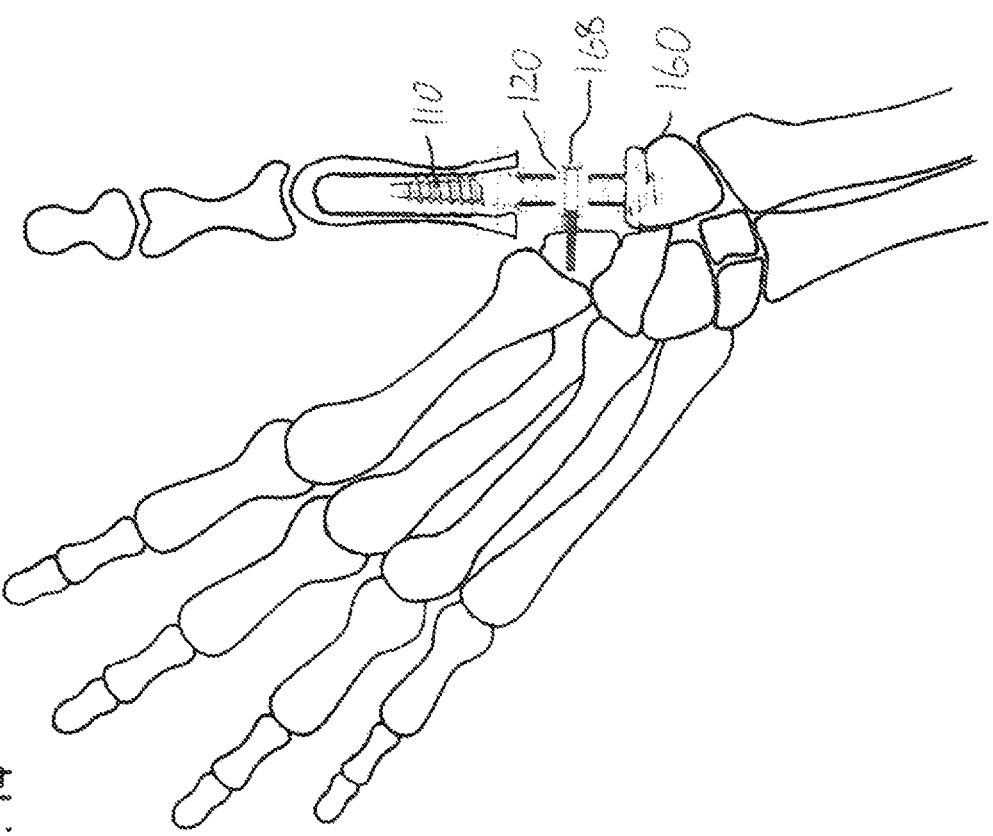
FIG. 14 is a schematic skeletal view of a human hand illustrating deployment of a prosthesis according to the teachings of a further aspect of the present invention for replacing joints in a human hand after removal of a trapezium.

Turning now to FIGS. 14 and 15, depending upon the degree of damage or deterioration of the trapezium, it may in some cases be necessary to remove a major part, or the entirety, of the trapezium. It is noted that the natural properties of the joints between the scaphoid and the trapezium and between the trapezium and the first metacarpal have similar mechanical properties, whereas the trapezium is essentially immobile relative to the trapezoid. One particular aspect of the present invention takes advantage of this observation by using the trapezoid to anchor an intermediate block, effectively serving as a prosthetic trapezium, and employs two of the aforementioned flexible bridging structures (of any of the disclosed types) to bridge between this intermediate block and the bone-anchoring blocks fixed to the scaphoid and the first metacarpal. One such example is illustrated in FIGS. 14 and 15.

Specifically, in this example, the second rigid block (120) that forms a joint with first rigid block (110) and flexible bridging structure (130) is an intermediate block of the prosthesis, which further includes a third rigid block (160) having a bone anchor portion (162) for fixation within the second bone (here, the scaphoid) and a third head portion (164) to remain projecting from the second bone. A second flexible bridging structure (166) is configured to bridge between the second rigid block (120) and the third rigid block (160).

Second rigid block (120) is in this case preferably rigidly anchored to the trapezoid, such as through a bone screw (168).

The structure and function of each of the two flexible joints, i.e., between rigid blocks (110) and (120) and between rigid blocks (120) and (160), are preferably according to one or other of the embodiments described in detail above. Tightenable bone-contact flanges are only provided on the sides of the joints abutting the metacarpal and scaphoid bones, while attachment of the bridging structures to the intermediate block (120) is typically via pre-formed permanent connection, such as by welding.

This aspect of the present invention is considered to be of particular significance as a method for forming a joint in the human hand after removal of a trapezium, where the method includes the steps of:
(a) rigidly anchoring a first block to a first metacarpal;
(b) rigidly anchoring a second block to a trapezoid;
(c) rigidly anchoring a third block to a scaphoid;
(d) providing a flexible bridging structure between said first block and said second block so as to form a first joint; and
(e) providing a flexible bridging structure between said second block and said third block so as to form a second joint.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. A prosthesis for replacing a joint between a first bone and a second bone in a human hand or foot, the prosthesis comprising:
   (a) a first rigid block comprising a bone anchor portion for fixation within the first bone and a first head portion to remain projecting from the first bone;
   (b) a second rigid block comprising a second head portion;
   (c) a flexible bridging structure comprising a helical spring deployed to bridge between said first head portion and said second head portion, said helical spring oriented such that a central axis of said helical spring is substantially aligned with a central axis of said bone anchor portion; and
   (d) a first rigid projection extending from said first head portion along the inside of said helical spring and a second rigid projection extending from said second head portion along the inside of said helical spring, said first and second rigid projections deployed within an internal volume of said helical spring so as to limit an extent of shear deformation applied to said helical spring.

2. The prosthesis of claim 1, wherein said first and second projections have convexly-curved lateral surfaces.

3. The prosthesis of claim 1, wherein said first and second projections extend towards each other so as to together span a majority of an unsupported length of said helical spring between said first and second head portions.

4. The prosthesis of claim 1, wherein said at least one shear-limiting element comprises a tether anchored to both said first head portion and said second head portion.

5. The prosthesis of claim 1, wherein said second rigid block further comprises a bone anchor portion for fixation within the second bone.

6. The prosthesis of claim 5, wherein the prosthesis is configured for forming a joint between a first metacarpal and a trapezium.

7. The prosthesis of claim 1, wherein said second rigid block is an intermediate block of the prosthesis, the prosthesis further comprising:
   (a) a third rigid block comprising a bone anchor portion for fixation within the second bone and a third head portion to remain projecting from the second bone; and
   (b) a second flexible bridging structure configured to bridge between said second rigid block and said third rigid block.

8. The prosthesis of claim 7, wherein the prosthesis is configured for forming a joint between a first metacarpal and a scaphoid after removal of a trapezium.

9. The prosthesis of claim 8, wherein said second block is configured for rigid anchoring to a trapezoid.

10. The prosthesis of claim 1, wherein there is a space within said helical spring between said first and second projections.

11. The prosthesis of claim 1, wherein said helical spring is the only element of the prosthesis connecting between said first head portion and said second head portion.

12. A prosthesis for replacing a joint between a first bone and a second bone in a human hand or foot, the prosthesis comprising:
   (a) a first rigid block comprising a bone anchor portion for fixation within the first bone and a first head portion to remain projecting from the first bone;
   (b) a second rigid block comprising a second head portion;
   (c) a flexible bridging structure configured to bridge between said first head portion and said second head portion, said flexible bridging structure comprising a helical spring for attachment to said first head portion; and
   (d) a flange element including a flange,
   wherein said first head portion is configured for insertion into a first end of said helical spring, and wherein said flange element has a central bore for deployment around said helical spring, an outside surface of said first head portion and said central bore of said flange element being configured to lock said helical spring therebetween.

13. The prosthesis of claim 12, wherein said central bore has a helical groove configured for engaging an outside surface of coils of said helical spring, said flange element being displaceable relative to said bone anchor by threaded motion along said helical spring.

14. The prosthesis of claim 12, wherein an outside surface of said first head portion has a peripheral recess for receiving at least an end coil of said helical spring, and wherein said central bore of said flange element is configured to trap said end coil of said helical spring within said recess.

15. The prosthesis of claim 12, wherein said flange element is configured to be displaceable relative to said bone anchor so that, after fixation of said bone anchor within the first bone, said flange is displaced until said flange comes into contact with the first bone, thereby distributing forces transferred through the prosthesis over a contact surface of said flange against the first bone.

16. The prosthesis of claim 15, wherein said flange element is one of a set of at least two flange elements usable interchangeably to engage said outer surface of said coils of said helical spring, said at least two flange elements differing from each other in an axial distance from said flange to an end of said central bore.

17. A prosthesis for replacing a joint between a first bone and a second bone in a human hand or foot, the prosthesis comprising:
   (a) a first rigid block comprising a bone anchor portion for fixation within the first bone and a first head portion to remain projecting from the first bone;
   (b) a second rigid block comprising a second head portion;
   (c) a flexible bridging structure configured to bridge between said first head portion and said second head portion; and
   (d) a flange element including a flange,
   wherein said flange element is configured to be displaceable relative to said bone anchor so that, after fixation of said bone anchor within the first bone, said flange is displaced until said flange comes into contact with the first bone, thereby distributing forces transferred through the prosthesis over a contact surface of said flange against the first bone, and wherein said flexible bridging structure comprises a helical spring for attachment to said first head portion, wherein said first head portion is configured for insertion into a first end of said helical spring, and wherein said flange element has a central bore for deployment around said helical spring.

18. The prosthesis of claim 17, wherein said central bore has a helical groove configured for engaging an outside surface of coils of said helical spring, said flange element being displaceable relative to said bone anchor by threaded motion along said helical spring.

19. The prosthesis of claim 17, wherein an outside surface of said first head portion and said central bore of said flange element are configured to lock said helical spring therebetween.

20. The prosthesis of claim 17, wherein an outside surface of said first head portion has a peripheral recess for receiving at least an end coil of said helical spring, and wherein said central bore of said flange element is configured to trap said end coil of said helical spring within said recess.

21. The prosthesis of claim 17, wherein said flange element is one of a set of at least two flange elements usable interchangeably to engage said outer surface of said coils of said helical spring, said at least two flange elements differing from each other in an axial distance from said flange to an end of said central bore.

\* \* \* \* \*